United States Patent [19]

Heeg et al.

[11] Patent Number: 4,923,816
[45] Date of Patent: May 8, 1990

[54] GASSING INCUBATOR

[75] Inventors: Hubert Heeg, Frankfurt; Hans-Peter Werner, Grosskrotzenburg; Manfred Fenner, Kleinkahl; Olaf Schmidt, Isenburg, all of Fed. Rep. of Germany

[73] Assignee: W. C. Heraeus GmbH, Hanau, Fed. Rep. of Germany

[21] Appl. No.: 340,891

[22] Filed: Apr. 19, 1989

[30] Foreign Application Priority Data

May 6, 1988 [DE] Fed. Rep. of Germany ....... 3815528

[51] Int. Cl.⁵ .............................................. F27D 11/00
[52] U.S. Cl. .................................... 435/284; 219/401; 219/407
[58] Field of Search ................. 219/401, 407; 435/284

[56] References Cited

U.S. PATENT DOCUMENTS 4,572,427 2/1986 Selfridge et al. .................... 219/407

FOREIGN PATENT DOCUMENTS 7707963 1/1979 Netherlands ........................ 219/401

Primary Examiner—Carroll B. Dority
Attorney, Agent, or Firm—Felfe & Lynch

[57] ABSTRACT

A gassing incubator for cultivating human or animal cells or tissues is known that has an inner case which can be closed by a door and is surrounded by a thermally insulating outer case. The outer case is spaced away from the side walls, back wall and roof of the inner case. Electrical heaters are disposed under the floor of the inner case and in the area of the side walls. The incubator has a means for humidifying the inner chamber atmosphere. To improved such an incubator so as to achieve a high relative humidity in the test chamber, and a rapid and uniform heating of the water, and to substantially prevent the formation of condensate on the inner wall of the case and enable the heating system to be made at low cost, the electrical heating elements are tubular heating elements which lie flat directly against the underside of the floor of the inner case, the humidifier is a pan containing water, and the tubular heating elements are bent upwardly at the side walls and back wall of the inner case such that they reach above the floor level of the inner case by the depth of the water bath, thus heating the transition area between the floor and the side walls and back wall.

7 Claims, 3 Drawing Sheets

GASSING INCUBATOR

BACKGROUND OF THE INVENTION

1. Field of the Invention

The present invention concerns a gassing incubator for cultivating human and animal cells or tissues. More particularly, this invention concerns incubators having an inner case which can be closed by an outside door. This inner case is surrounded by a thermally insulating outer case, the outer case being spaced away from the lateral walls, rear wall and roof of the inner case. Electrical heating elements are disposed under the floor of the inner case and in the lateral wall area. The incubator also has a means for humidifying the internal atmosphere

2. Discussion of Related Art

An incubator of this kind is disclosed, for example, in GB-A No. 231,259. Between the inner case and the outer case a one-piece tubular heating element is disposed which runs in a serpentine configuration through the two side walls and the floor. Both the walls and the floor of the inner case have openings through which the air in the interstitial space, heated by the tubular heating element, can circulate into the incubating chamber. The air flow between the central or incubating chamber and the interstitial space is produced by a blower in the rear wall which aspirates the air from the central chamber into a chamber at the rear of the incubator and returns it to the interstice through a bottom chamber. The central chamber can also be connected by an air duct to a refrigeration unit which has an additional blower as well as an evaporator.

To moisten the air in the central chamber of such incubators, two different kinds of humidifying means are used. In the one kind, water is evaporated from a water reservoir outside of the central chamber and the aerosol is fed to the central chamber. Another way of humidifying the central chamber air is to place a water reservoir directly in the central chamber where it is evaporated. Usually, a water pan is disposed on the floor of the central chamber and heated with an appropriate heating device which ca be placed directly in the water bath.

It is to be observed that the known incubators achieve widely varying results in regard to uniform temperature distribution along the inner walls of the incubator chamber. For example, incubators in which the temperature distribution in the inner case is irregular tend to form condensate on the colder areas of the wall, so that high humidities of 90% and up are very difficult to achieve.

SUMMARY OF THE INVENTION

An object of the present invention is to construct an incubator of the kind described above, such that a high relative humidity can be reached in the central chamber, the water can be heated rapidly and uniformly, the formation of condensate on the inner wall of the case will be largely prevented, and the heating system can be produced economically.

This object is achieved by using as the electrical heating elements tubular heaters which lie flat and directly against the outside of the bottom of the inner case, which has a humidifying device in the form of a pan containing water, and by bending these heating elements upwardly at the side walls and rear wall of the inner case such that they extend above the floor level of the inner case to a level slightly above the surface of the water bath, and thus heat the transition area between the bottom and the side walls and back wall.

By arranging the tubular heating elements on the floor and in the lower area of the side walls and back wall the heating of the water supply can be controlled. At the same time, however, the interstitial space between the inner case and the thermally insulated outer case is uniformly heated by the ascending hot air. The heating of the inner case walls by the convection in the interstitial space results in a uniform temperature distribution in the central chamber, so that no condensation is produced on the inner walls of the inner case. Furthermore, by the special arrangement of the tubular heating element or elements the corner areas of the inner case, i.e., the areas of transition between the floor and the lateral walls and back wall, are heated, the tubular heating elements being directly in contact with the bottom of the floor of the inner case, so that the water contained in a pan resting on the bottom of the inner case is heated directly. Unlike the tubular heating element disposed at the bottom of the case, the tubular heating elements in the area of the side walls and back wall are disposed so as to radiate freely, i.e., they should not be in contact with the case walls, so that no areas of elevated temperature will be produced. This is especially important in the side wall and back wall areas above the level of the water. Inasmuch as little or no condensate forms on the walls of the inner case, relative humidities can be reached and sustained at levels above 95%.

In the preferred embodiment, a pan that lies flat on the floor is used as the water source in order to achieve a direct transfer of heat to the water. This direct heat transfer can be enhanced by constructing the bottom of the inner case as the pan, for example: drawing the bottom of the inner case from a piece of high-grade steel. Depending on the size of the water supply required, the entire bottom of the central chamber can be a pan, thus providing a large evaporation surface.

The tubular heating elements that are used are preferably bent in a serpentine configuration or like a meander, so that they uniformly wrap around and heat the inner case, especially in the bottom rear corner areas of the inner case. In one preferred embodiment, two tubular heating elements are used. Each of these tubular heating elements is folded around one of the corner areas so that several loops of each tubular heating element ar provided in three planes at right angles to one another. To prevent condensation on the glass door, one heating element can be incorporated into the door to heat the door as a heating film or a resistance-heating wire.

BRIEF DESCRIPTION OF THE DRAWING

Additional details and features of the invention will be found in the description provided below of an embodiment represented in the drawing, wherein.

DETAILED DESCRIPTION OF THE PREFERRED EMBODIMENTS

Figure 1:
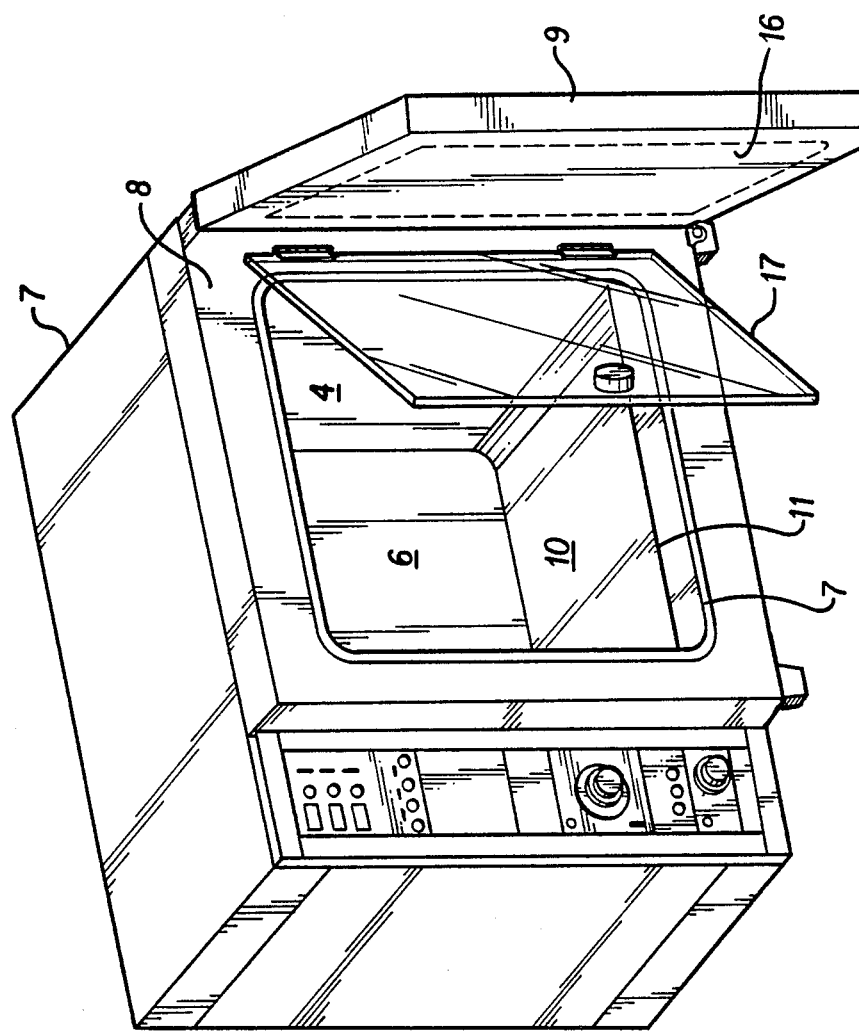
FIG. 1 is a perspective view of a gassing incubator.
Figure 2:
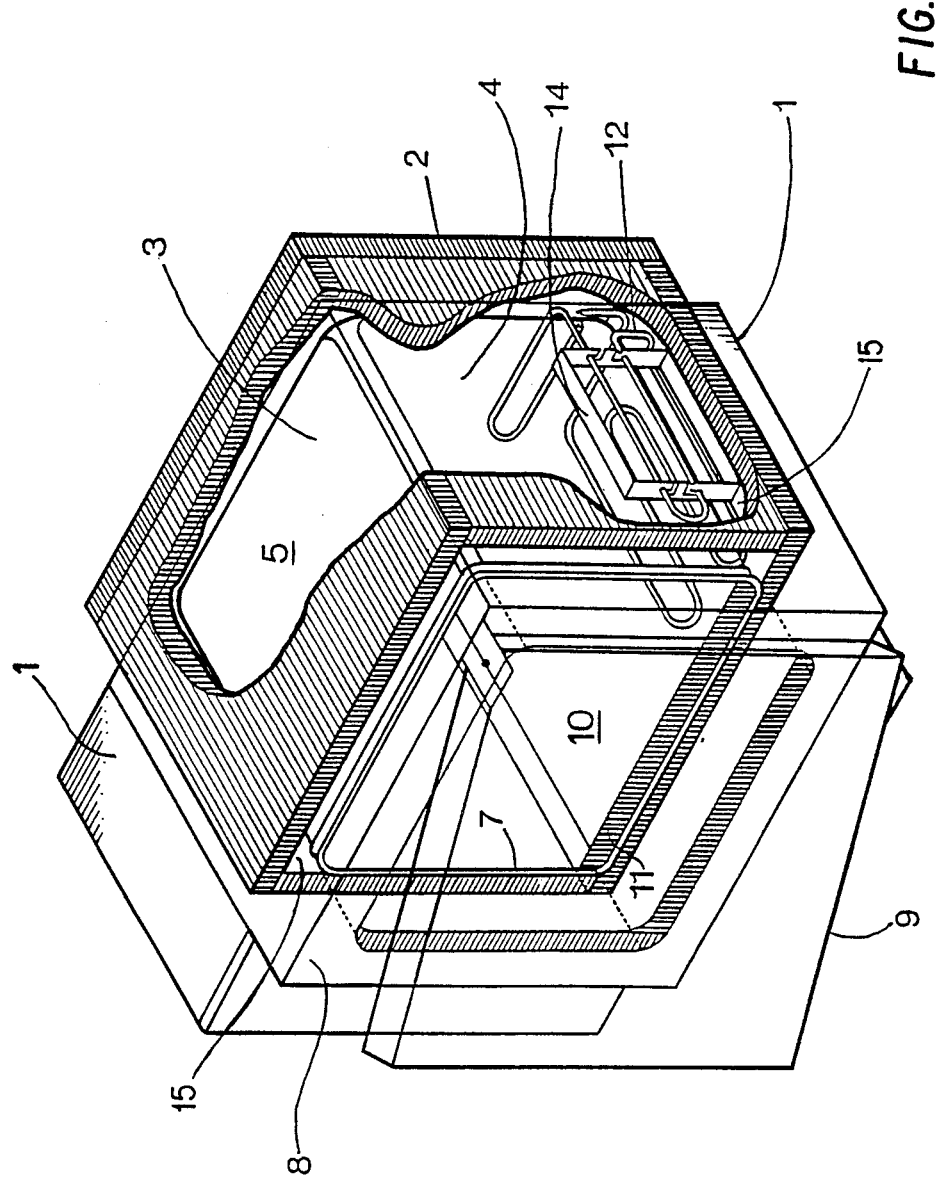
FIG. 2 is a cut-away view of a gassing incubator.
Figure 3:
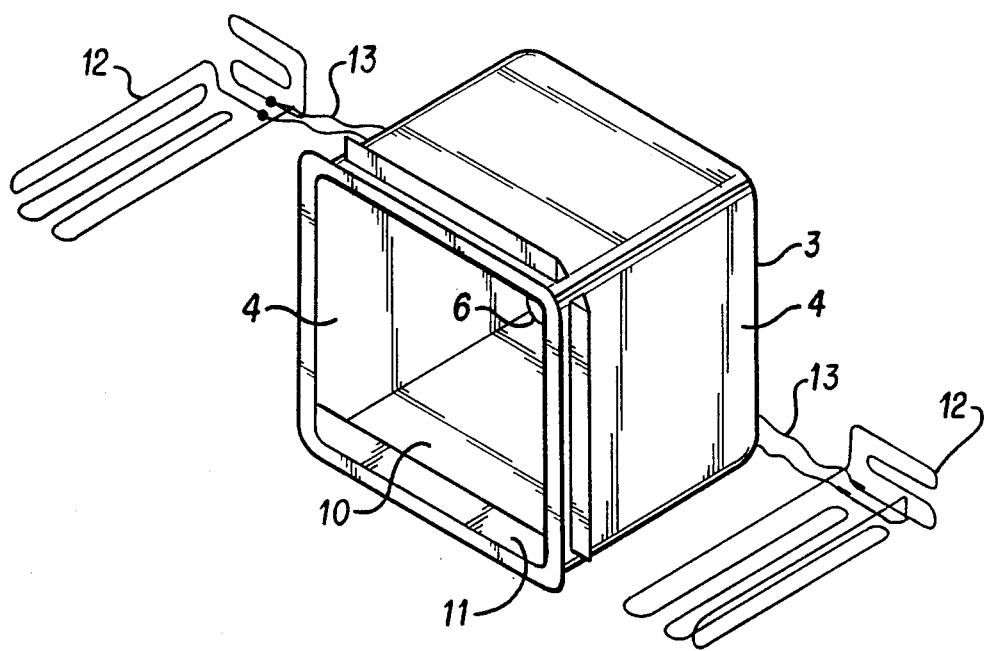
FIG. 3 shows an inner case like the one used in the incubator in accordance with FIG. 1, with two tubular heating elements associated with the inner case.

The incubator, as it is shown in FIGS. 1 and 2, has an outer case 1 which is lined on its inside with a self-supporting thermal insulating material 2. An inner case is inserted into the outer case 1 and is spaced away from the latter and from the inside of the thermal insulating board 2, so that an interstitial space is formed between the inner case 3 and the thermal insulating board 2, at least in the area of the side walls 4 and the top side 5. The back wall of the incubator, which is not seen in this front view, is also thermally insulated and spaced away from the back wall 6 of the inner case 3. Both the thermal insulating material 2 and the inner case 3 are represented in FIG. 2 as being backed slightly out of the outer case 1. The inner case has a sealing rim 7 around its margin, which reaches through the front frame 8 and sealingly engages a door 9, a glass door for example. A dam 11 is inserted into the bottom of the inner case at the opening so as to form a pan 10. This pan 10 can be filled with water approximately up to the top edge of the dam 11.

To heat the central chamber of the inner case 3, two tubular heating elements 12 are provided, which wrap around the floor of the inner case 3 and the lower area of the lateral walls 4 the back wall 6 in which the pan 10 is formed. Each of the two tubular heating elements is formed integrally in a serpentine configuration from a tube, two loops thereof being associated with the floor, one with the side wall 4, and two with the back wall 6. The three planes which are formed by these loops are perpendicular to one another. The two terminal ends 13 of each tubular heating element 12 are situated in the area of the middle of the back wall 6 so a to be easily accessible. The loops of the tubular heating element 12 terminate at the side wall 4 and back wall 6 such that the pan 10 will be sufficiently heated. Particularly the edges and the corner areas of the inner case 3 are heated by the two tubular heating elements 12. The tubular heating elements 12 which lie on the floor of the inner case 3, which simultaneously is the bottom of the pan 10 holding the supply of water, are spaced away from the side walls 4 and the back wall 6. At the side walls 4, and at the back wall also, if desired, the tubular heating elements are supported by a frame 14, of sheet metal for example, as it can be seen in FIG. 2. The water stored in the pan 10 is heated by the tubular heating elements 12 so as to evaporate; at the same time the interstitial space 15 formed between the inner case 3 and the thermal insulation 2 is uniformly heated by thermal convection.

The dam 11 is given a height of about 40 mm, so that the pan can be filled with water to a depth of 15 to 20 mm. For a cube-shaped central chamber with a volume of about 83 liters, the surface area of the water should be approximately 0.2 $m^2$, the volume of the interstitial space 15 in the area of the side walls about 9 liters, in the area of the roof about 5 liters and in the area of the back wall 6 about 7 liters, resulting in a total volume in the convection chamber or interstitial chamber 15 of about 21 liters. For an incubator with a useful volume of about 250 liters, the area of the water surface should be about 0.4 $m^2$, the water capacity about 5 to 6 liters, the volume of the interstitial space 15 at the side walls 4 about 21 liters, at the roof about 9 liters and at the back wall 6 about 15 liters. With these dimensions, and a tubular heating element 12 of corresponding design, which is to extend above a level of about 10 cm in the area of the side walls 4 and the back wall 6, an optimum evaporation of water and heating of the walls of the inner case 3 are obtained.

What is claimed:

1. A gassing incubator for cultivating human or animal cells or tissues, said incubator comprising:
   an inner case having a door;
   a thermally insulating outer case surrounding said inner case and disposed at a distance from side walls, a back wall and a roof of said inner case;
   electrical heating elements including at least one tubular heating body, said elements being disposed underneath a floor of the inner case in flat contact direct with the outer side of the floor of the inner case and angled upwardly in the area of the side walls and the back wall of the inner case such that they extend above the floor level of the inner case by the depth of a water bath on said floor and thus heat the area of transition between the bottom and side walls and the back wall in the area of the side walls; and
   means forming a pan accommodating said water bath for humidifying the inner chamber atmosphere.

2. A gassing incubator in accordance with claim 1, wherein the tubular heating bodies facing the side walls and the back wall (6) are spaced away from these walls.

3. A gassing incubator in accordance with claim 1 wherein the means forming the pan is positioned at the back wall and the side walls at least in the rearward area adjoining the back wall.

4. A gassing incubator in accordance with claim 1 wherein the floor of the inner case is constructed as a pan.

5. A gassing incubator in accordance with claim 1 wherein the tubular heating body is bent in a serpentine form.

6. A gassing incubator in accordance with claim 5 wherein a one-piece tubular heating body is associated with each rearward, lower corner area of the inner case, said body having serpentine loops running in three planes that are perpendicular to one another.

7. A gassing incubator in accordance with claim 1 wherein a heating body is disposed in the door.

* * * * *